US005695794A

United States Patent [19]
Stark et al.

[11] Patent Number: 5,695,794
[45] Date of Patent: Dec. 9, 1997

[54] USE OF 25-HYDROXYCHOLECALCIFEROL IN A DIETARY SUPPLEMENT PROCESS FOR AMELIORATING THE EFFECTS OF TIBIAL DYSCHONDROPLASIA IN POULTRY WHILE MAINTAINING WEIGHT GAIN

[75] Inventors: Leonard Stark, Naperville; James G. Yarger, St. Charles; Samuel Perry, Winfield, all of Ill.

[73] Assignee: Amoco Corporation, Chicago, Ill.

[21] Appl. No.: 513,228

[22] Filed: Aug. 10, 1995

[51] Int. Cl.$^6$ .................. A61K 15/02; A61K 31/59; A23K 1/16; A23K 1/18
[52] U.S. Cl. .................. 426/2; 426/73; 426/807; 424/442
[58] Field of Search .................. 426/2, 73, 807; 424/442

[56] References Cited

U.S. PATENT DOCUMENTS

| | | |
|---|---|---|
| 3,639,596 | 2/1972 | DeLuca et al. ............. 424/236 |
| 3,653,921 | 4/1972 | Buhler et al. . |
| 4,267,191 | 5/1981 | Baker et al. ............. 424/285 |
| 5,043,170 | 8/1991 | Borenstein et al. ............. 426/73 |
| 5,154,925 | 10/1992 | Edwards, Jr. ............. 424/422 |
| 5,316,770 | 5/1994 | Edwards, Jr. ............. 424/442 |
| 5,366,736 | 11/1994 | Edwards, Jr. ............. 424/442 |

OTHER PUBLICATIONS

Edwards et al., *J. Nutr.*, 13:1568–1575 (1983).
Edwards et al., *Poultry Sci.*, 73:228–294 (1994).
Edwards, *J. Nutr.*, 120:1054–1061 (1990).
Edwards et al., *Poultry Sci.*, 71:2041–2055 (1992).
Rennie et al., *British J. Nutr.*, 69:809–816 (1993).
Farquharson et al., *J. Bone Miner. Res.*, 8:1081–1088 (1993).
Edwards, *J. Nutr.*, 119:647–652 (1989).
McNutt et al., *J. Nutr.*, 103:681–689 (1973).
Cantor et al., *Poultry Sci.*, 57:1123–1124 (1978).
Ward, *Feedstuffs*, 67:13–15 (1995).
Yarger et al., *Poultry Sci.*, 74:1159–1167 (Jul. 1995).
McNaughton, *Feedstuffs*, 27:13–14, 22 (1990).

*Primary Examiner*—Donald E. Czaja
*Assistant Examiner*—Choon P. Koh
*Attorney, Agent, or Firm*—Welsh & Katz, Ltd.

[57] ABSTRACT

A process for ameliorating the effects of tibial dyschondroplasia while maintaining weight gain in poultry is disclosed as are a supplemented poultry feed and a feed supplement concentrate. The process contemplates feeding the bird with a poultry feed that contains 35 to 350 micrograms of 25-hydroxycholecalciferol per kilogram of feed. The supplement feed is used in the above process, whereas a feed supplement concentrate comprises a comestible diluent containing about 0.05 to about 100 mg of 25-hydroxycholecalciferol per gram of concentrate.

14 Claims, 1 Drawing Sheet

USE OF 25-HYDROXYCHOLECALCIFEROL IN A DIETARY SUPPLEMENT PROCESS FOR AMELIORATING THE EFFECTS OF TIBIAL DYSCHONDROPLASIA IN POULTRY WHILE MAINTAINING WEIGHT GAIN

DESCRIPTION

1. Technical Field

The present invention relates to the amelioration of avian tibial dyschondroplasia by dietary supplementation, and more particularly to the use of a relatively large amount of 25-hydroxycholecalciferol as a dietary supplement for poultry to decrease the occurrence and severity (ameliorate) of tibial dyschondroplasia, while maintaining weight gain in the treated birds.

BACKGROUND OF THE INVENTION

Tibial dyschondroplasia ("TD") is a skeletal abnormality that occurs in rapidly growing animals such as chickens, turkeys, ducks and the like. The abnormality is characterized by an unmineralized, unvascularized mass of cartilage located in the proximal ends of the tibiotarsus and the tarsusmetatarsus. The cartilage extends from the growth plate into the metaphysis. In fowl, tibial dyschondroplasia usually appears between three and eight weeks of age.

In some chickens and turkeys, the prehypertrophic cartilage persists into adulthood and is restricted to the posterior medial portion of the proximal tibiotarsal bone, and the birds remain clinically normal. An incidence of 10 to 30 percent of birds with subclinical dyschondroplasia is common in many flocks.

In the more severe cases of TD, the abnormal tissue occupies the whole metaphysis of the proximal tarsometatarsal bone. Birds with these more severe lesions may be lame, with bowing of the affected bones. These birds can have difficulty walking and are prone to falling down, causing injury and decreasing growth rate. The disease also increases the death rate of animals during the growth period. Further, many of the birds suffering from the disease develop breast blisters and leg deformities that result in hemorrhages.

Tibial dyschondroplasia increases the percentage of carcasses downgraded or condemned in processing plants, which results in decreased profits for the processor. When flocks of birds have a high incidence of TD, the crooked legs can interfere with the shackling of the fowl during processing and can actually cause mechanical problems in operating the processing line where the slaughtered fowl are conveyed on machines which handle the birds by their legs. Fowl with TD have insufficient leg strength to be carried in this manner.

Several dietary factors such as the levels of phosphorus and calcium have been found to have major effects on the expression of TD. High phosphorus levels in feed lead to accentuated development of lesions, whereas, high calcium levels in feed tend to retard development of the lesions. Edwards et al., *J. Nutr.*, 13:1568 (1983).

Vitamin $D_3$ (cholecalciferol ["CC"]) and certain of its hydroxylated derivatives, when added to feed, have been found useful in treating TD in various poultry species. For example, Edwards' U.S. Pat. No. 5,154,925, No. 5,316,770 and No. 5,366,736 teach use of several dihydroxy and dihydroxy-dideuterocholecalciferol compounds (collectively referred to as vitamin $D_3$ derivatives) for treating and preventing this condition. These compounds are said to be useful at a concentration of 0.10 to 20 micrograms per kilogram of bird body weight per day or at between 1 and 10 micrograms per kilogram of feed per day.

U.S. Pat. Nos. 5,316,770 and 5,366,736 also teach the use of 25-hydroxycholecalciferol ("25-HCC") for treating or preventing tibial dyschondroplasia. In addition, these two patents teach that feeding more than 10 micrograms per kilogram (µg/kg) of any of the vitamin $D_3$ derivatives tends to cause a decrease in growth rate.

Further studies by Edwards and co-workers and other groups have focused on the requirements of birds for ultraviolet light [Edwards et al., *Poultry Sci.*, 73:288–294 (1994)] and on the use of 1,25-dihydroxycholecalciferol [Edwards, *J. Nutr.*, 120:1054–1061 (1990); Edwards et al., *Poultry Sci.*, 71:2041–2055 (1992); Rennie et al., *British J. Nutr.*, 69:809–816 (1993); Farquharson et al., *J. Bone Miner. Res.*, 8:1081–1088 (1993)].

An earlier paper, Edwards, *J. Nutr.*, 119:647–652 (1989), discloses the use of vitamin $D_3$ (CC) along with 25-hydroxycholecalciferol (25-HCC) or 1,25-dihydroxycholecalciferol (1,25-DHCC) in the presence or absence of disulfiram. Vitamin $D_3$ was used at 27.5 µg/kg [1100 international chick units ("ICU")/kg], whereas each of the vitamin $D_3$ derivatives was used at 10 µg/kg. This paper reported no response from use of 25-HCC, whereas there was said to be a dramatic response to the use of 1,25-DHCC.

Early work [McNutt et al., *J. Nutr.*, 103:681–689 (1973)] reported the usefulness of low doses of vitamin $D_3$ (CC), 25-HCC and 1,25-DHCC on enhancing growth in chicks fed on a diet deficient in vitamin D. The chick groups were fed 52 up to 1820 pmoles of one of CC, 25-HCC or 1,25-DHCC every 48 hours in this study. Even at the highest level, this amount was less than the maximal dosage suggested by Edwards, above.

Cantor et al., *Poultry Sci.*, 57:1123–1124 (1978) also reported on the efficacy of CC and 25-HCC fed at low doses to broilers. There, feeding of 2.50 µg/kg of 25-HCC was said to significantly improve weight and feed/gain compared to feeding vitamin $D_3$. The problem of bone breakage due to processing animals fed with supplements of CC or 25-HCC was not alleviated. Breast blister percentages for birds fed with either supplement were similar.

The various hydroxylated vitamin $D_3$ derivatives are metabolites of vitamin $D_3$ itself and can be prepared by several well known procedures. For example, 25-HCC can be prepared as described in U.S. Pat. No. 4,310,467 and No. 3,565,924, whereas 1,25-DHCC can be prepared as described in U.S. Pat. No. 4,310,467 and No. 3,697,559. The 1,25-DHCC derivative can be prepared from 25-HCC.

Inasmuch as 25-HCC can be a precursor for 1,25-DHCC, it would be advantageous if the precursor 25-HCC could be used to ameliorate the effects of TD in poultry if bird weight gains were not seriously affected. The disclosures that follow illustrate that 25-HCC can be so used to reduce the incidence and/or severity of TD, while not seriously effecting growth rates.

BRIEF SUMMARY OF THE INVENTION

The present invention relates to a process for ameliorating the effects of tibial dyschondroplasia while maintaining weight gain in poultry. That process comprises feeding those birds a poultry feed that contains 35 to about 350 micrograms per kilogram of feed, and more preferably about 50 to about 100 µg/kg, of exogenously added 25-hydroxycholecalciferol. A supplemented poultry feed that comprises a poultry feed supplemented with 35 to about 350 micrograms per kilogram (µg/kg) of feed, and preferably about 50 to about 100 µg/kg, of exogenously added 25-hydroxycholecalciferol is also contemplated that can be a solid or liquid, aqueous supplement containing the amount of 25-HCC.

The present invention has general benefits and advantages.

One benefit is that 25-hydroxycholecalciferol can be used to ameliorate the effects of tibial dyschondroplasia.

An advantage of the invention is that 25-hydroxycholecalciferol, when used as a feed supplement, does not inhibit bird growth and can enhance weight gain and feed efficiency.

Still further benefits and advantages of the invention will be apparent to a worker of ordinary skill from the description that follows.

BRIEF DESCRIPTION OF THE DRAWING

In the drawing comprising a portion of this disclosure.

DETAILED DESCRIPTION OF THE INVENTION

Figure 1:
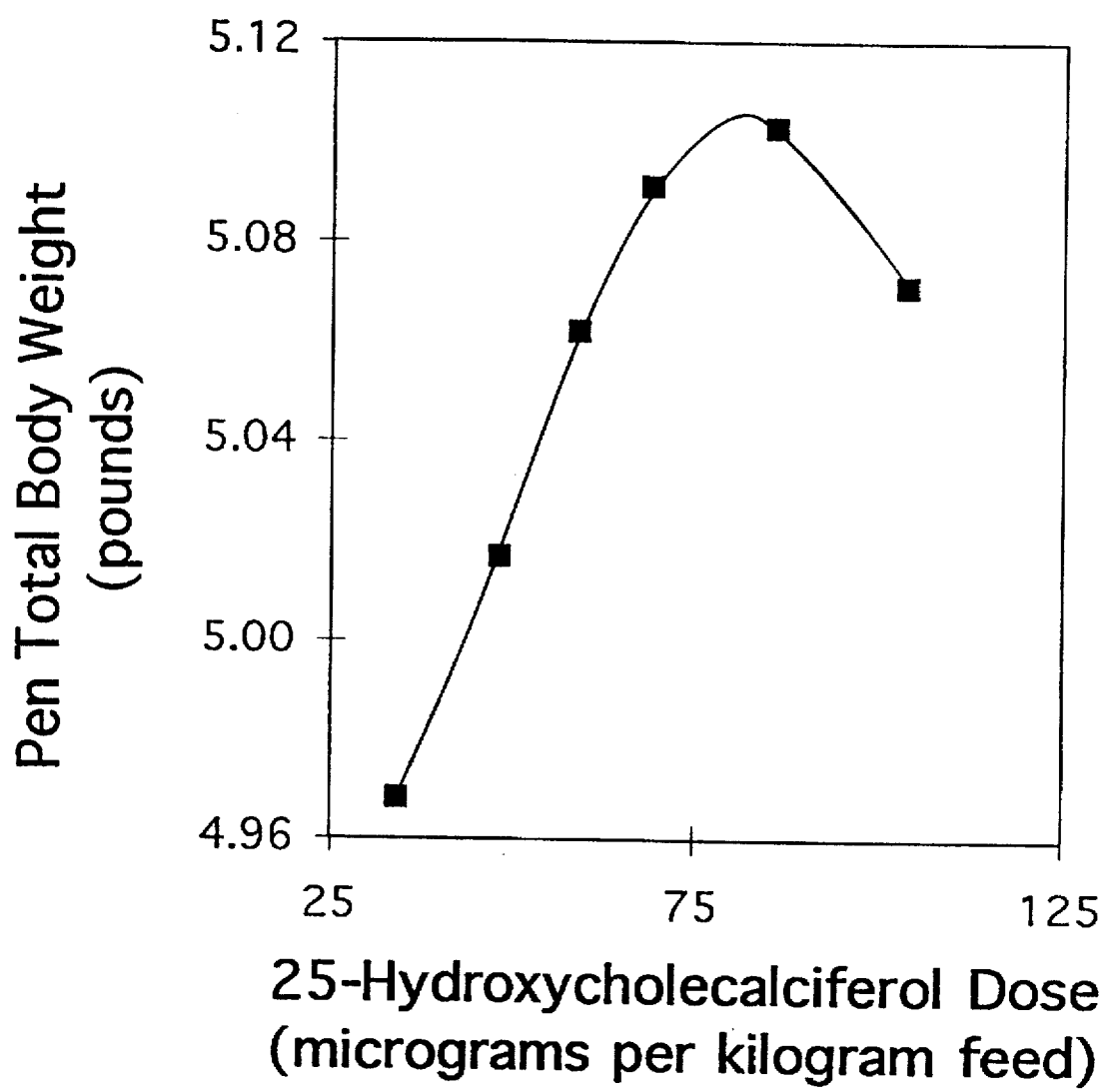
FIG. 1 is a graph that illustrates weight gain of broiler chickens as a function of supplementing 25-hydroxycholecalciferol.

The present invention relates to a process for ameliorating the effects of; i.e., reducing the incidence and/or severity of, tibial dyschondroplasia in poultry while maintaining weight gain in the birds. In accordance with this process, poultry such as chickens, turkey, ducks, geese, guinea fowl and the like are fed with a feed that contains 35 to about 350 micrograms per Kilogram (µg/kg) of feed of exogenously supplied; i.e., added, 25-hydroxycholecalciferol (25-HCC).

From the disclosures of Edwards in (1) his U.S. Pat. No. 5,316,770 and No. 5,366,736 that teach that use of a vitamin $D_3$ derivative such as 25-HCC in an amount of excess of 10 µg/kg of feed tends to decrease the rate of weight gain, and (2) his paper in *J. Nutr.*, 119:647–652 (1989) that teaches 25-HCC fed along with 27.5 µg/kg feed of vitamin $D_3$ (CC) had no effect on TD, it was quite surprising that 25-HCC in fact could be used effectively to reduce the incidence and/or severity of TD in poultry, while not seriously affecting growth rates of the treated birds.

As will be seen from the data that follow, use of 25-HCC and vitamin $D_3$ (CC) in broilers that were bred to have a high incidence of TD resulted in a drastic reduction in the incidence of TD. Thus, birds fed on feed containing only vitamin $D_3$ (2750 ICU/kg feed) exhibited an incidence of 11.8 percent TD, whereas only 2.4 percent of the birds fed on a similar diet also containing 344.5 µg/kg feed of 25-HCC developed TD, as did 4.2 percent of birds fed with 68.9 µg/kg feed of 25-HCC. For those same birds, the severity values for TD lesions were 3.8, 0.8 and 2.1, respectively, on a 5 point scale in which 5 is the most severe. These dramatic results were obtained with weight gains that were substantially identical when measured at 13, 28 and 42 days into the study. These results are highlighted in Ward, *Foodstuffs*, 67:13–15 (1995).

Another study carried out by one of the inventors and co-workers, Yarger et al., *Poultry Sci.*, 74:1159–1167 (1995) whose disclosures are incorporated by reference, utilizes ten feeding trials involving over 36,000 broilers. There, 25-HCC supplements present at an amount of about 35 µg/kg through about 105 µg/kg were used.

Here, average body weights for birds whose feed was supplemented with 25-HCC were greater than the average body weights for birds whose feed was supplemented with CC (vitamin $D_3$) in nine of the ten trials, with no difference in the tenth trial. A dose-dependent relation between the amount of 25-HCC present in the supplemented feed and weight gain was shown, with about 50 to about 70 µg/kg being the optimal amount of supplementing 25-HCC. Similar dose dependencies were noted for feed efficiency and breast meat yield. Percentage mortality was lower in six of the ten studies for birds whose diets were supplemented with 25-HCC, but the differences were not significant.

In a feed trial carried out for the inventors at a commercial poultry complex with a commercial chicken breed (Peterson×Arbor Acres), birds fed on feed supplemented with vitamin $D_3$ (2750 ICU/g of feed) exhibited a 21 percent incidence rate of TD at an age of about 21–35 days. Birds fed on vitamin $D_3$ (CC) supplemented feed additionally supplemented with 25-HCC (68.9 g/kg feed) had TD incidence levels of 13.9 percent, 10.3 and 11.4 percents after three different postings, with no decrease in weight gain (6 random birds were analyzed from each of 18 different farms to provide 108 birds per posting). Anecdotal reports from plant managers indicated a lessening in the amount of breast blistering observed with this use of 25-HCC. These results are thus contrary to the results reported in Cantor et al. *Feed Sci.*, 57:1123–1124 (1978) using a much lower concentration of 25-HCC.

Thus, the results here indicate that use of 25-HCC as described above as a feed supplement to poultry provides protection from or amelioration of the effects of TD (lessened incidence and severity) without adversely affecting weight gain of the poultry so treated, and such supplementation can actually increase weight gain. Thus, weight gains with supplementation of 25-HCC are greater or within about 10 percent of weight gains of similar birds fed the same diet without 25-HCC, so that weight gains of the treated birds are maintained to be about those exhibited by control birds.

The 25-HCC utilized can be from any source and can be prepared as discussed previously. The 25-HCC is more preferably utilized in an amount of about 50 to about 100 µg/kg of feed. An amount of about 50 to about 70 µg/kg of feed has been found to be optimal in the present studies.

The poultry feed used can also be from any source and can be any usually used food. The contemplated food can be solid or liquid with the 25-HCC supplement being emulsified or dispersed in a bird's drinking water or present in the solid portion of a bird's diet.

Typical poultry feeds are based on wheat, soybean meal or corn or combinations thereof, along with additives such as limestone for calcium and dicalcium phosphate to supply phosphorus, vitamins, minerals, antibiotics and other materials as recommended by the U.S. Department of Agriculture, the National Research Council and poultry raising associations.

The feed (diet regimen) used usually changes from a "starter" (0–3 weeks) to a "grower" (3–6 weeks) and then to a "finisher" (6–7 weeks) mixture and can also include an initial "pre-starter" and/or late "withdrawal" formulations. These feeds differ primarily in protein content as fed for 21, 21 and 7 days from start to finish, with the 25-HCC being added to each type of feed. These types of unsupplemented feeds are well know to skilled workers.

The 25-HCC can be added to the poultry feed by any usually used method. Typically, here, the 25-HCC is mixed with the feed by simple physical mixing of the solid feed ingredients with "beadlets" containing the added 25-HCC.

Thus, small beads are prepared having diameters of about 30 to about 55 microns by a spraying process. The sprayed composition is a molten solution of a desired amount of 25-HCC dissolved in hydrogenated vegetable oil such as hydrogenated cotton seed oil, wheat-germ oil, safflower oil, soybean oil and the like, that also can contain mono- and diglycerides such as those prepared from hydrogenated soybean mono- and diglycerides, cottonseed mono- and diglycerides and the like, as well as citric acid and 2,6-di-tert-butyl-4-methylphenol (BHT) as antioxidants. Other antioxidants such as ethoxiquin, vitamin E and the like can also be used, as is well known. The molten mixture is sprayed at a temperature of about 160° F. (about 70° C.) into a cyclonic airstream of a spray chiller such as available from Niro, Inc., Columbia, Md. to produce the beadlets that solidify on cooling. The cooled beadlets are dusted with a anticaking agent such as fumed silica, calcium phosphate, powdered starch or cellulose as are well known to form the beadlets that are preferably added to the feed as supplement. An exemplary beadlet contains about 10 to about 100 milligrams of 25-HCC per gram (mg/g) and preferably at about 10 to about 50 mg/g.

The beadlets are typically further diluted by admixture with commercially available rice hulls as an inert comestible carrier to a concentration of about 140 mg/kg to form a feed supplement concentrate. Thus, the invention contemplates a further embodiment that is a concentrate or premix containing about 0.05 to about 100 mg/g of 25-HCC dissolved or dispersed in or on comestible diluent. A preferred concentrate contains about 0.10 to about 15 mg/g of 25-HCC. Exemplary diluents include the rice hulls discussed before. Those diluents also include solid and liquid fats such as a hydrogenated vegetable oil was noted above, as well as oleaginous materials that are liquids or semi-solids at room temperature. Exemplary latter materials include babassu oil, cocoa butter, coconut oil, cotton seed oil, rapeseed oil, soybean oil and the like.

The feeds can be simple admixtures of the various ingredients. Poultry feeds are typically pelletized forms of the various ingredients and pellets are a preferred form of a completed, 25-HCC supplemented feed. Methods for forming pellets from feed ingredients useful herein are well known in the art, and will not be gone into here.

A contemplated feed supplement can also be provided via a bird's water supply. When so provided, the supplementing 25-HCC can be provided as an emulsion or as a stable dispersion of particles.

In the case of an emulsion, 25-HCC itself or a before-described 25-HCC-containing beadlet is dissolved in a vegetable oil such as cotton seed, soybean or safflower oils and suitably emulsified as with a polysorbate emulsifier such as Tween® –20, –40, –60 or –80 or a similar edible dispersing agent as is well-known. An exemplary emulsion contains about 30 to about 50 milligrams of 25-HCC per ounce of emulsion.

In an exemplary stable dispersion, about 3 to about 5 grams of the before-described 25-HCC-containing beadlets (about 30–50 milligrams of 25-HCC) are dispersed per ounce of water with the aid of a dispersing agent such as carboxymethylcellulose, xanthan gum, an alginate or the like as are also well-known. Passage of the mixture so produced through a high speed dispersion mill provides a stable aqueous dispersion of micron-sized 25-HCC-containing particles.

In a further embodiment, vitamin $D_3$ is also added to the poultry feed mixture. Vitamin $D_3$ is added in an amount of about 1100 to about 3300 ICU (international chick units) per kilogram of feed, and is commercially available from Hoffmann-LaRoche, Nutley, N.J.

The following examples are offered to further illustrate, but not limit the present invention.

EXAMPLE 1

Comparison of the Effects of Combined 25-hydroxycholecalciferol (25-HCC) and Cholecalciferol (CC) on Tibial Dyschondroplasia in Chickens In studies carried out for the inventors under the direction of Drs. Gaynet McDaniel and D. A. Roland of the Poultry Science Dept., Auburn University, Auburn, Ala., Ross broiler chickens (1500 birds) were fed 25-HCC or CC supplemented diets and analyzed for tibial dyschondroplasia (TD). Two strains of birds having different natural incidences of TD were used. Day-old Ross broiler chickens (750 birds) selected over several generations for a high natural incidence of tibial dyschondroplasia ("TD") were used for the "high TD" studies. Day-old random-bred Ross broiler chickens (750 birds) having a comparatively low natural incidence of TD were used for the "low TD" studies.

The chickens were wing-banded, and allocated at random to deep-litter floor pens in groups of 50. Three diet regimens (described below) were provided to each of the two strains of chickens (high TD and low TD), with a total of 5 groups per set (250 of each strain of chicken per diet regimen).

The chickens were provided with standard commercial broiler diets, in this case the corn/soy-based feed shown in Table 1. The starter diet was provided from day 1 to day 19. The grower diet was provided from day 20 to day 40. The finisher diet was provided from day 41 to day 49.

TABLE 1

Typical rations, by ingredient*

| INGREDIENT NAME | STARTER AMOUNT | GROWER AMOUNT | FINISHER AMOUNT |
|---|---|---|---|
| Corn ground-B, 0/14 | 5652.0 | 8140.0 | 8720.0 |
| Soybean meal-48.3% | 3222.0 | 2730.0 | 2200.0 |
| Meat and bone 50% | 300.0 | 500.0 | 410.0 |
| Fat | 402.0 | 415.0 | 400.0 |
| Phosphate/defluorinated | 74.0 | 82.0 | 50.0 |
| Limestone | 40.0 | 40.0 | 40.0 |
| Salt | 32.0 | 33.0 | 35.0 |
| DL-Methionine 99% | 19.0 | 21.0 | 14.4 |
| Vitamin $D_3$-3000[1] | 18.4 | 18.4 | 3.1 |
| Bio-Cox[1] | 10.0 | 10.0 | 0.0 |
| Choline chloride | 8.2 | 7.9 | 4.0 |
| Trace minerals | 7.5 | 7.5 | 4.5 |
| Selenium Premix | 5.0 | 5.0 | 2.5 |
| Bacitracin MD-50[2] | 5.0 | 2.5 | 2.5 |
| Broiler vitamin premix | 5.0 | 5.0 | 8.4 |
| TOTAL BATCH: | 10000.4 | 10001.3 | 9999.9 |

*Ingredients are shown in units of one hundred times the weight percent of each relative to the total.
[1]Available from Hoffmann-LaRoache, Inc., Nutley, NJ.
[2]Available from A.L. Laboratories, Ft. Lee, NJ.

The control group ("control") was provided with a feed supplement of CC at a concentration of 55 µg/kg feed (2.2 MIU/ton; where "MIU" is one thousand international units, also known as international chick units, "ICU"). The first study group ("low 25-HCC") was provided with a feed supplement of CC at a concentration of 55 µg/kg feed (2.2 MIU/ton feed) and 25-HCC at a concentration of 68.9 µg/kg feed (2.75 MIU/ton feed). A second study group ("high 25-HCC") was provided with a feed supplement of CC at a concentration of 55 μg/kg feed (2.2 MIU/ton-feed) and 25-HCC at a concentration of 344.5 μg/kg (13.75 MIU/ton feed).

A constant record of chicken mortality was kept for each group. The feed consumption was determined every 7 days. The body weight was measured on days 13, 28 and 42. The feed efficiency was calculated on days 13, 28 and 42. Tibial dyschondroplasia was determined on days 28 and 42 by Lexiscope. The yield data were collected from 5 randomly chosen males and 5 randomly chosen females for each study group. Blood samples of two randomly chosen chickens per group were analyzed on days 28 and 42 for 25-HCC concentration in the serum.

There was no statistically significant difference in body weights for the control and study groups for both strains of chicken. Both high and low concentrations of 25-HCC supplements did not affect growth, compared to the CC-supplemented control.

A TD incidence rate of about 94 percent was observed for the high TD control at six weeks. At the same time, the high TD chickens fed both "low" and "high" 25-HCC supplemented diets exhibited decreased TD incidence (down to 88 and 87.6 percents incidence, respectively, P<0.05), as well as decreased TD severity.

The low TD chickens had an average incidence rate of 11.8 percent for the control groups, which is a typical rate of incidence for commercial flocks. For the low TD chickens, both low and high 25-HCC supplementation resulted in decreased incidence (P<0.001) and severity of TD. The TD incidence dropped to 4.2 percent with supplements of the low 25-HCC concentration. The TD incidence dropped to 2.4 percent with supplements of the high 25-HCC concentration.

The TD was half as severe for the chickens that were fed the low 25-HCC supplemented diets compared to the CC supplemented diets. The TD severity was reduced by 75 percent for the chickens that were fed the high 25-HCC supplemented diets compared to the CC supplemented diets.

The data indicate that the effectiveness of 25-HCC supplements both in lowering the incidence and severity of TD is related to dose, with higher concentrations of supplement being more effective in the range studied.

EXAMPLE 2

Comparison of Separate Dietary Supplementation With 25-hydroxycholecalciferol (25-HCC) and Cholecalciferol (CC) in Broiler Chickens The data presented in this Example are from a series of 10 feeding trials involving over 36,000 chickens, and are described in greater detail in Yarger, et al., *Poultry Science*, 74:1159–1167 (1995), which is incorporated herein by reference. These feeding trials were carried out for the inventors at PARC Institute Inc., Easton, Md. and Colorado Quality Research, Inc., Fort Collins, Colo. under the direction of Drs. J. L. McNaughton and C. L. Quarles, respectively.

Briefly, the vitamin $D_3$ derivative, 25-hydroxycholecalciferol (25-HCC) was provided in the form of stabilized food grade hydrogenated vegetable oil-based beadlets containing butylated hydroxytoluene and citric acid as discussed herein before. The formulated beadlets, containing 50 mg of 25-HCC/g of beadlets, were further diluted into a premix containing 138 mg of 25-HCC/kg using commercially available rice hulls as an inert carrier. A similar premix containing 138 mg vitamin $D_3$(CC)/kg was obtained from Hoffmann-LaRoche (Nutley, N.J. 07110).

The birds were grown in floor pens consistent with industry practice, with 50 to 90 birds per pen, with a bird density of 0.7 square feet per bird (0.065 square meters per bird). Two common commercial strains of broiler birds were used in these feeding trials, Arbor Acres×Arbor Acres and Peterson×Arbor Acres.

The birds were provided with commercial starter, grower and finisher rations containing 23, 20 and 18 percent protein. The starter rations were provided from about day 1 to day 20. The grower rations were provided from about day 21 to day 39. The finisher rations were provided from about day 40 to day 49. The calcium and available phosphorus levels ranged from 0.8 to 1 percent and 0.35 to 0.46 percent in all diets, respectively. All other nutrients were added according to 1994 National Research Council recommendations. All grower and finisher diets were pelletized consistent with industry practice.

The concentrations of vitamin $D_3$ or 25-HCC supplements ranged from one-half to one and a half times 69 μg/kg, which is the standard concentration for CC used in the industry [(McNaughton, *Feedstuffs*, August 27:13–15 (1990)].

A per pen basis was used for measures of average body weights and for calculations of feed conversion efficiency. The feed conversion efficiency was calculated by dividing the weight of the feed per pen by the weight of the birds per pen. The adjusted feed conversion efficiency included the weight of the birds that had died during the study in the calculation.

Mortality of the birds was monitored twice a day, removing birds that had died. Birds were also removed for humane reasons. The removed birds were necropsied. A random selection of four to twelve birds per pen was subjected to carcass evaluation. Breast meat was expressed as a percentage of live body weight.

Vitamin D metabolite serum concentrations were monitored in a subset of the studies. Serum 25-HCC concentrations were measured after acetonitrile extraction by radio-immunoassay using a commercially available kit from INCSTAR [Hollis et al., *Clin. Chem.*, 39:529–533 (1993)]. Serum 1,25-DHCC concentrations were measured by radioreceptor assay. [Reinhardt et al., *J. Clin. Endocrinol. Metabol.*, 58:91–98 (1984); Hollis, *Clin. Chem.*, 32:2060–2063 (1986)].

Statistical analysis was performed using the appropriate algorithm of the ANOVA statistical analysis program. One-way ANOVA were used to compare different CC and 25-HCC levels, although some studies also included additional experimental factors. Experimental errors for statistical tests were pooled across all treatments. The significance level was computed using a one-sided least significant difference test [Daniel, in *Biostatistics*, 6th ed., John Wiley, New York, p. 295 (1995)]. The sample size for each treatment mean is the number of pens for each of the treatments.

Results

In 9 of the 10 studies, the average body weight was greater in birds whose diets were supplemented with 25-HCC than in those whose diets were supplemented with the same amount of CC (P≤0.05). The birds supplemented with 25-HCC weighed an average of 0.04±0.03 kg more than birds supplemented with the same amount of CC. In 7 of the 10 studies, adjusted feed efficiency was lower (better) in birds fed 25-HCC than in those treated with vitamin $D_3$. In three of the eight studies in which it was evaluated, the percentage of breast meat was greater in birds treated with 25-HCC.

Mortality was variable in all of the studies and there were no abnormalities related to 25-HCC supplements. Mortality was lower for birds fed 25-HCC than birds fed CC in six of the ten studies, but there was no significant relationship between the percentage mortality and the dietary level of 25-HCC.

The average body weight increased and adjusted feed efficiency decreased with increasing dietary level of 25-HCC up to approximately 50 to 70 µg/kg feed. The unadjusted feed efficiency showed a similar trend.

The serum 25-HCC levels increased with increasing vitamin $D_3$ or 25-HCC dietary supplements. The serum concentration of 25-HCC was about twice as high when the supplement was 25-HCC as when the supplement was CC.

The serum levels of the metabolite 1,25-DHCC were similar for the same amounts of vitamin $D_3$ or 25-HCC in the diet. The 1,25-DHCC serum levels did not vary with alterations in levels of dietary supplements of vitamin $D_3$ (CC) or 25-HCC in the range assayed.

The data clearly document a consistent effect of 25-HCC to increase body weight and decrease feed efficiency (either adjusted or unadjusted) in broiler chickens grown under simulated commercial conditions. The absolute magnitude of the changes in weight (0.04 kg, 1.7 percent) and feed efficiency (0.026 adjusted or 0.039 unadjusted) are small but real. As a result of the size of the industry ($7 \times 10^9$ birds in the United States in 1993, consuming $32 \times 10^6$ tons of feed), small percentage changes are significant.

The studies also clearly show a dose-response relationship between dietary 25-HCC and improvement in weight gain and feed efficiency. FIG. 1 shows a plot of weight gain versus 25-HCC supplement amount for birds from three of those ten studies. Such a dose-response relationship was not observed in preliminary studies with vitamin $D_3$.

There was a significant increase in percentage breast meat in two of the ten feeding trials in spite of these being only a small increase in body weight in the birds fed 25-HCC. Substitution of 25-HCC for vitamin $D_3$ as a source of dietary vitamin $D_3$ had no adverse effects on survival and no adverse effects were detected upon gross pathologic examination of the dead birds.

There were positive correlations between serum 25-HCC concentrations and body weight ($r=0.45$, $P<0.01$) and breast meat ($r=0.33$, $P<0.01$) and an inverse correlation with adjusted feed efficiency ($r=0.42$, $P<0.01$), with no correlation being observed between serum 1,25-DHCC and these variables.

The foregoing description and the examples are intended as illustrative and are not to be taken as limiting. Still other variations within the spirit and scope of this invention are possible and will readily present themselves to those skilled in the art.

We claim:

1. A process for ameliorating the effects of tibial dyschondroplasia while maintaining weight gain in poultry that comprises feeding said poultry a poultry feed that contains 35 to about 350 micrograms of exogenously added 25-hydroxycholecalciferol per kilogram of feed.

2. The process according to claim 1 wherein said feed contains about 50 to about 100 micrograms of 25-hydroxycholecalciferol per kilogram of feed.

3. The process according to claim 1 wherein said poultry feed also contains about 1100 to about 3300 ICU of vitamin $D_3$.

4. The process according to claim 1 wherein said poultry are chickens.

5. A process for ameliorating the effects of tibial dyschondroplasia while maintaining weight gain in chickens that comprises feeding said chickens a chicken feed that contains about 50 to about 100 micrograms of exogenously added 25-hydroxycholecalciferol per kilogram of feed.

6. The process according to claim 5 wherein said chicken feed also contains about 1100 to about 3300 ICU of vitamin $D_3$.

7. A supplemented poultry feed that comprises a poultry feed supplemented with 35 to about 350 micrograms of exogenously added 25-hydroxycholecalciferol per kilogram of feed.

8. The supplemented feed according to claim 7 wherein said 25-hydroxycholecalciferol is present at about 50 to about 100 micrograms per kilogram of feed.

9. The supplemented feed according to claim 7 that additionally contains about 1100 to about 3300 ICU of vitamin $D_3$.

10. The supplemented feed according to claim 7 wherein said feed is a chicken feed.

11. The supplemented feed according to claim 7 wherein said 25-hydroxycholecalciferol is emulsified or dispersed in water.

12. A poultry feed supplement concentrate that comprises a comestible diluent containing about 0.05 to about 100 milligrams of 25-hydroxycholecalciferol per gram of feed supplement concentrate.

13. The poultry feed supplement concentrate according to claim 12 wherein said diluent includes rice hulls.

14. The poultry feed supplement concentrate according to claim 12 wherein said diluent includes a fat.

* * * * *